United States Patent [19]

Kojima

[11] Patent Number: 4,773,186

[45] Date of Patent: Sep. 27, 1988

[54] PORTABLE POLISHING UNITS FOR DENTAL INSTRUMENTS

[75] Inventor: Norio Kojima, Tokyo, Japan

[73] Assignee: G-C Dental Industrial Corp., Tokyo, Japan

[21] Appl. No.: 60,160

[22] Filed: Jun. 10, 1987

[30] Foreign Application Priority Data

Jul. 9, 1986 [JP] Japan .................. 61-159598

[51] Int. Cl.$^4$ .............................................. B24B 7/00
[52] U.S. Cl. ...................................... 51/125; 51/102; 51/128; 51/238 R
[58] Field of Search ............... 51/102, 125, 109 R, 51/72 R, 128, 71, 125.5, 98.5, 170 R, 170 PT, 170 T, 238 T, 285, 218 R, 208, 210, 218 P, 98 R, 98.5, 238 R

[56] References Cited

U.S. PATENT DOCUMENTS

| | | | |
|---|---|---|---|
| 328,256 | 8/1885 | Scott | 51/238 R |
| 483,042 | 9/1892 | Brown | 51/238 R |
| 2,297,306 | 9/1942 | Kousin | 51/125 |
| 2,435,642 | 2/1948 | Bates | 51/125 |
| 2,578,309 | 12/1951 | Kroczek | 51/125 |
| 2,663,976 | 12/1953 | Jacoby | 51/125 |
| 3,084,486 | 4/1963 | Orciani | 51/125 |

Primary Examiner—Frederick R. Schmidt
Assistant Examiner—Lawrence Cruz
Attorney, Agent, or Firm—Oblon, Fisher, Spivak, McClelland & Maier

[57] ABSTRACT

A portable polishing unit for dental instruments is characterized by comprising a base member; a motor mounted thereon and driven by a dry cell; a rotary grindstone assembly fixed to the motor through a grindstone rod of a round shape and including a grindstone disc positioned in opposition to the motor, having a diameter larger than that of the grindstone rod and planar on its end face; a supporting member mounted on the base member at a position adjacent to the side of the grindstone disc which does not face the motor, and having a plane face extending in parallel with the upper face of the base member and having a length larger than the diameter of the grindstone disc; and a supporting plate mounted on the base member in the vicinity of the side edge of the supporting member, the supporting plate including a groove for supporting the root of working means extending from a grip of a dental instrument.

11 Claims, 3 Drawing Sheets

PORTABLE POLISHING UNITS FOR DENTAL INSTRUMENTS

BACKGROUND OF THE INVENTION

1. Field of the Invention

The present invention relates to a portable polishing unit for dental instruments such as scalers for removing dental calculi, which can accurately and rapidly polish worn-out edge surfaces of the working means thereof.

2. Statement of the Prior Art

In most cases, working means having an edge surface or surfaces on one side or both sides are attached to dental instruments for filling and forming dental composite resins or cements in and on proximal surfaces of teeth or tooth cavities. Polishing is required for such dental instruments having edged working means, since their edge surfaces wear away be use.

Hitherto, polishing for such edged working means of the dental instruments has been carried out by applying them to a plane portion of a grindstone of a rectangular parallelpipal shape at a predetermined angle and moving the grindstone or the instruments.

In most cases, however, the edged working means of the dental instruments have their edge surfaces curved or one of their edge surface arched. Thus, considerable skill, labor and time are required to polish such curved edge surface or arched edge surface with the grindstone of a rectangular parallelpipal shape, since all of the polishing surfaces of such grindstones are planar.

In order to eliminate the disadvantage of the conventional method for polishing the edge surfaces of the working means of dental instruments, a polishing device including a grindstone driven and rotated by a motor has been proposed in, for instance, Japanese Utility Model Publication of the application No. 53-1672. Even with this device, it is not possible to effect polishing in a state where the edge surfaces of the working means of dental instruments are precisely and stably located on the polishing face of the rotating grindstone. As a result, one problem arises that the edge surfaces of the working means of dental instruments are so excessively polished that their service life shortens. Another problem also arises that the edge surfaces of the working means of dental instruments are excessively polished by the rotating grindstone so that burrs occur thereon.

SUMMARY OF THE INVENTION

As a result of various studies made by the present inventor, it has been found that the aforesaid problems are solved by the provision of a portable polishing unit for dental instruments which is similar to the conventional polishing device in that a grindstone rotated by a motor is used for polishing the edge surfaces of the working means of dental instruments, but which is characterized by the structure wherein a motor driven by a dry cell is used as that motor, and polishing is effected using as the working section of a rotary grindstone assembly rotated by the motor one planar of a grindstone disc forming a part of the assembly, not the circumferential section of the rotary section forming a part of the assembly; and a supporting member is located in opposition to the grindstone disc of the grindstone assembly and is mounted on a base member at a position adjacent to the side of the grindstone disc which does not face the motor, the supporting member having a plane face extending in parallel with the upper face of the base member and having a length larger than the diameter of the grindstone disc.

More specifically, according to one aspect of the present invention, there is provided a portable polishing unit for dental instruments comprising in combination:

a base member, a motor mounted thereon and driven by a dry cell, a rotary grindstone assembly fixed to the motor and including a grindstone disc positioned in opposition to the motor and planar on its end face, and a supporting member mounted on the base member at a position adjacent to the side of the grindstone disc which does not face said motor, and having a plane face extending in parallel with the upper face of the base member and having a length larger than the diameter of the grindstone disc.

According to anther aspect of the present invention, there is provided a portable polishing unit for dental instruments, comprising in combination:

a base member, a motor mounted thereon and driven by a dry cell, a rotary grindstone assembly fixed to the motor through a grindstone rod of a round shape and including a grindstone disc positioned in opposition to the motor, having a diameter larger than that of the grindstone rod and planed on its end face, a supporting member mounted on the base member at a position adjacent to the side of the grindstone disc which does not face said motor, and having a plane face extending in parallel with the upper face of the base member and having a length larger than the diameter of the grindstone disc, and a supporting plate mounted on the base member in the vicinity of the side edge of the supporting member, the supporting plate including a groove for supporting the root of working means extending from a grip of a dental instrument.

With the portable polishing unit according to the present invention, a dental instrument can be polished while its portion adjacent to the working means to be polished is stably positioned and placed on the plane face of the supporting member. Further, by constructing the rotary grindstone assembly of the polishing unit from the grindstone disc section planar on its end face and the grindstone rod section of a round shape which is located on the side of the grindstone disc section facing the motor and has a diameter smaller than that of the grindstone disc section, it is possible to remove burrs occurring on the arched or edge surface of the thus polished working means of the dental instrument. Still further, if the base member is provided at a position adjacent to the side edge of the supporting member with the supporting plate including the groove for supporting the root of the working means extending from the grip of the dental instrument, it is possible to support the root of the working means of the dental instrument in that groove. At the same time, while the portion of the working means adjacent to its edge surface is stably supported on the aforesaid plane face, the edge surface of the working means of the dental instrument can be caused to abut upon the polishing face of the grindstone disc section of the rotary grindstone assembly for assuring satisfactory polishing.

BRIEF DESCRIPTION OF THE DRAWINGS

A portable polishing unit for dental instruments in accordance with the present invention will now be described in greater detail, by way of example, with reference to the accompanying drawings, in which.

DETAILED DESCRIPTION OF THE PREFERRED EMBODIMENTS

Figure 1:
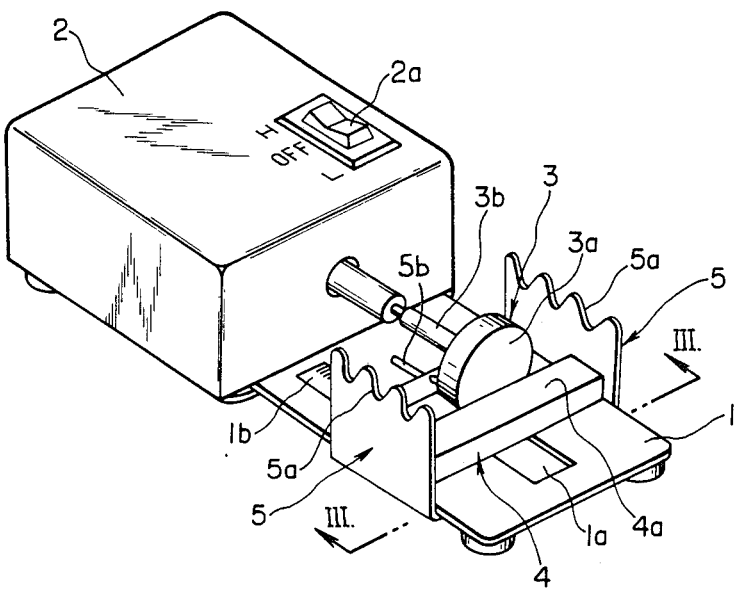
FIG. 1 is a perspective view of one embodiment of the portable polishing unit for dental instruments in accordance with the present invention.

Referring to the drawings, there is shown a base member 1 having thereon a casing 2 which houses a motor driven by a dry cell. A switch 2a for turning on or off the motor is provided on a given position of the casing 2 (e.g., on the front end position of the upper face of the casing 2, as illustrated). It is preferred that the on/off switch 2a is of the changeover type capable of rotating the motor at either high or low speed, since the degree of polishing of working means 6b of a dental instrument 6 is adjustable.

A rotatable grindstone assembly shown generally at 3 includes a rod section 3b formed of a grindstone rod of a round shape and secured to the motor and a disk section 3a having a diameter larger than that of the rod section 3b and formed of a grindstone disc that is planar on its end face. The rod section 3b is provided to remove burrs occurring on the working means 6b of the dental instrument 6, it preferably has a diameter of 4 to 6 mm with the configuration of such working means 6b in mind.

A supporting member shown generally at 4 is mounted on the base member 1 at a position which is located in opposition to and in the vicinity of the side of the disk section 3a of the grindstone assembly 3 which does not face the motor, and has its upper face 4a is planar and extends in parallel with the upper face of the base member 1, The upper face 4a has a length longer than the diameter of the disk section 3a of the grindstone assembly 3.

Figure 2:
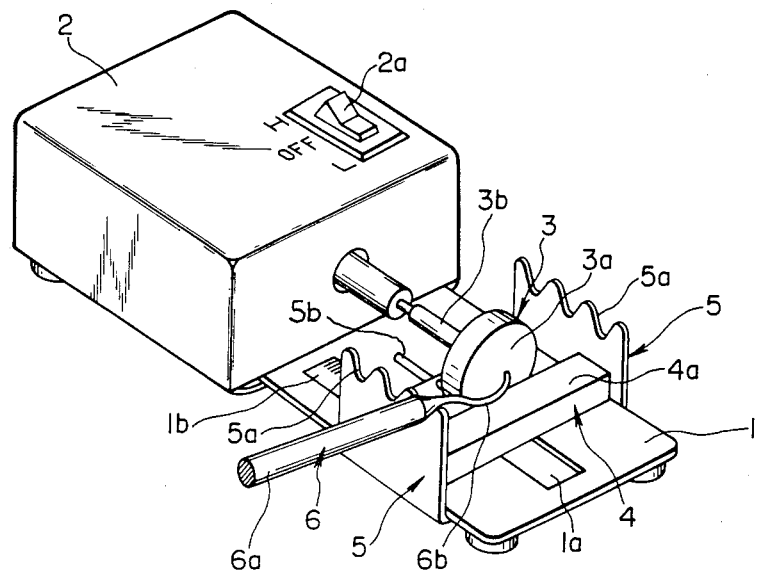
FIG. 2 is a perspective view illustrating a dental instrument which is being polished with the portable polishing unit according to the present invention.
Figure 3:
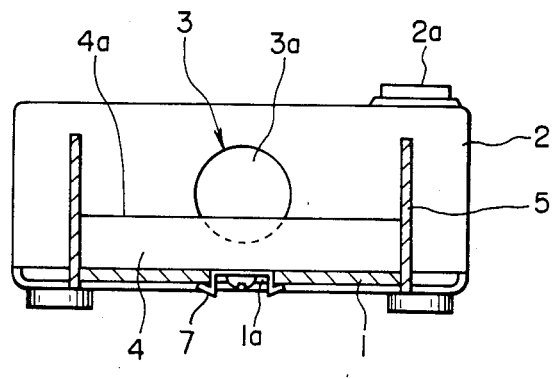
FIG. 3 is an enlarged section taken along the line III—III of FIG. 1, FIGS. 4 and 5 are perspective views of other embodiments of the supporting plate.

In the embodiment illustrated in FIGS. 1 and 2, an elongated slot 1a is formed in the base member 1, and a leaf spring (see FIG. 3) movable in the slot 1a and bearing on the lower face of the base member 1 is fixedly provided below the supporting member 4 so as to allow the supporting member 4 to move in the axial direction of the motor along the slot 1a.

A supporting plate shown generally at 5 is located in the vicinity of the side edge of the supporting member 4 and mounted on the base member. A groove 5a is formed in the supporting plate 5 for supporting the root of the working means 6b extending from a grip 6a of the dental instrument 6. It is preferred that the supporting plate 5 is provided with a plurality of grooves 5a and is of a structure capable of moving along the sides of the base member 1, as is the case with the supporting member 4. In the embodiment illustrated in FIGS. 1 and 2, the side of the supporting plate 5 facing the casing 2 holds the base member 1 from its both sides and also from above and below, and the thus held portion is provided with a springy, downward projection 5b, whereby the supporting plate 5 is stopped at a position to which it is moved along the sides of the base member 1.

Figure 4:
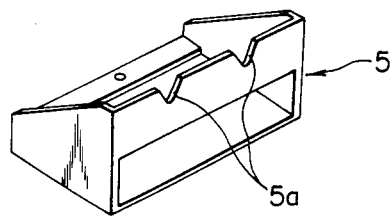
Figure 5:
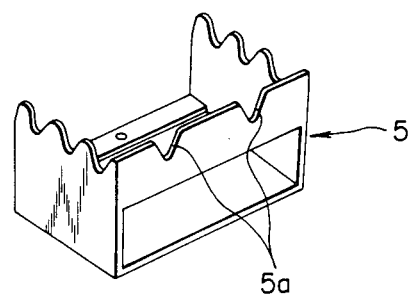
Figure 6:
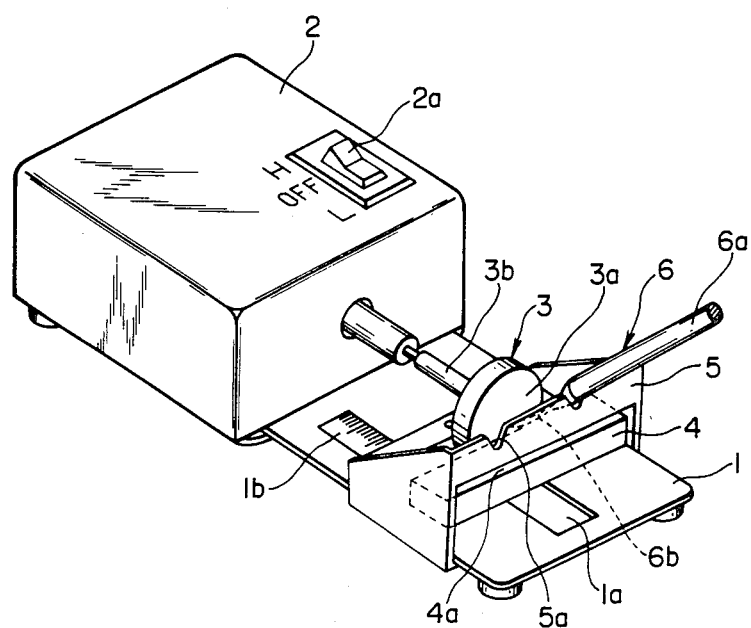
FIG. 6 is a perspective view showing a dental instrument which is being polished with the invented portable polishing unit having the supporting plate of FIG. 4 attached thereto.

Referring to the supporting plate 5, its grooves 5a may be located in the vicinity of the edges of both sides of the supporting member 4, as illustrated in FIG. 1. Alternatively, the grooves 5a may be located in the vicinity of the edge of the side of the supporting member 4 which does not face the motor, as illustrated in FIG. 4. Still alternatively, the grooves 5a may be provided both in the vicinity of the edges of both sides of the supporting member 4 and in the vicinity of the edge of the side of the supporting member 4 which does not face the motor, as illustrated in FIG. 5. Where the supporting plate 5 is of the structure capable of moving along the sides of the base member 1, it is preferred that the base member 1 is calibrated at a scale 1b so as to confirm its moving position.

The invented portable polishing unit of the aforesaid structure operates as follows.

First, the rotary grindstone assembly 3 is attached to the driving shaft of the motor housed in the casing 2. In this case, if the grindstone assembly 3 includes the rod section 3b of 4 to 6 mm in diameter, then that rod section 3b is secured to the driving shaft of the motor. Subsequently, the supporting member 4 is located at a given position on the base member 1, and it is mounted there. In this case, where the supporting member 4 is movable in the axial direction of the motor shaft along the elongated slot 1a formed in the base member 1, it may be moved along that slot 1a to the given position. Also, where the supporting plate 5 is mounted on the base member 1 and is designed to be movable along both sides of the base member 1, it may be moved in such a manner that its grooves 5a are located at given positions.

In this manner, the stage for preparing for polishing the dental instrument 6 is finished.

Then, the grip 6a of the dental instrument 6 to be polished is grasped to locate the given portion thereof on the supporting member 4. While the edge surface of the working means 6b to be polished abuts upon the plane face of the disc section 3a of the grindstone assembly 3, the switch 2a is put on to drive the motor. Thus, the edge surface of the working means 6b of the dental instrument 6 can be polished. When polishing an arcuate portion of the working means 6b of the dental instrument 6, satisfactory polishing of that portion can be achieved by turning the grip 6a of the dental instrument 6 in the aforesaid state. Such operations are considered easy for workmen skilled in polishing. For unskilled workmen, however, it is more convenient to use the portable polishing unit for dental instruments according to the present invention wherein the base member 1 is mounted thereon with the supporting plate 5 located in the vicinity of the side edges of the supporting member 4 and including the grooves 5a for supporting the root of the working means 6b extending from the grip 6a of the dental instrument 6, since the root of the working means 6b of the dental instrument 6 is limited in respect of its position by the grooves 5a and securely held thereby to assure easy polishing. Further, if burrs occur on the thus polished working means 6b in this polishing process, or if a curved edge surface of the working means 6b is polished, polishing may be carried out while that working means 6b abuts upon the rad section 3b of the rotary grindstone assembly 3.

With the portable polishing unit according to the present invention, the edge surface of the working means 6b of the dental instrument can be polished, while its portion adjacent to the working means 6b to be polished is stably positioned and placed on the upper face 4a of the supporting member 4. Futher, by constructing the rotary grindstone assembly 3 of the polishing unit from the grindstone disc section 3a that is planar on its end face and the grindstone rod section 3b of a round shape which is located on the side of the grindstone disc section 3a facing the motor and has a diameter smaller than that of the grindstone disc section 3a, it is possible to prevent burrs from occurring on the edge face of the thus polished working means 6b of the dental instrument 6. It is also possible to easily polish the working means 6b, even when it is in an arched form, with the grindstone rod section 3b having a smaller diameter. Thus, the polishing of dental instruments is ensured with high accuracy. Still further, if the base member 1 is provided at a position adjacent to the side edge of the supporting member 4 with the supporting plate 5 including the grooves 5a for supporting the root of the working means 6b extending from the grip 6a of the dental instrument 6, it is possible to polish the edge surface of the working means 6b, while the root of the working means 6b extending from the grip 6a of the dental instrument 6 to be polished is more stably supported by two points defined by the upper planar face 4a of the supporting member 4 and the groove 5a in the supporting plate 5. Still further, various dental instruments 6 can be polished in a preferable state by designing either the supporting member 4 to be movable in the axial direction of the motor along the elongated slot 1a formed in the base member 1 or the supporting plate 5 to include a plurality of grooves 5a and to be movable along the sides of the base member 1. Still further, it is possible to adjust the degree of polish for the dental instrument 6 designing the motor to be driven at either high or low speed by the on/off switch 2a.

As mentioned in the foregoing, the portable polishing units for dental instruments according to the present invention are light in weight, simple in structure, inexpensive to manufacture, and easy to carry, and they thus make great contributions to dentistry.

While the present invention has been described with reference to some specific embodiments, it is to be understood that many changes or modifications may be made without departing from the scope and spirit of the present invention, as defined in the appended claims.

I claim:

1. A portable polishing unit for dental instruments, said portable polishing unit comprising in combination:
   (a) a base member;
   (b) a motor mounted on the upper face of said base member and driven by a dry cell;
   (c) a rotary grindstone assembly fixed to said motor through a grindstone rod section of a round shape and including a grindstone disc section positioned on the opposite side of said grindstone rod section from said motor, said grindstone disc section having a diameter larger than that of said grindstone rod section and being planar on its face facing away from said motor;
   (d) a supporting member mounted on the upper face of said base member at a position adjacent to said face of said grindstone disc section facing away from said motor, said supporting member having a planar upper face extending in parallel with the upper face of said base member for supporting a first portion of a dental instrument while the dental instrument is being ground by said face of said grindstone disc section facing away from said motor, said upper face of said supporting member having a length longer than the diameter of said grindstone disc section; and
   (e) a supporting plate mounted on said base member in the vicinity of the side edge of said supporting member, said supporting plate including at least one groove located above said upper face of said base member for supporting a second portion of the dental instrument while the dental instrument is being ground by said face of said grindstone disc section facing away from said motor.

2. A polishing unit as claimed in claim 1, wherein said supporting plate including said at least one groove is mounted on said base member in the vicinity of the edges of both sides of said supporting member.

3. A polishing unit as claimed in claim 1, wherein said supporting plate including said at least one groove is mounted on said base member in the vicinity of the edge of the side of said supporting member facing away from said motor.

4. A polishing unit as claimed in claim 1, wherein said supporting plate including said at least one groove is mounted on said base member in the vicinity of the edges of both sides of said supporting member and the edge of the side of said supporting member facing away from said motor.

5. A polishing unit as claimed in any one of claims 1-4, wherein said supporting member is movable in the axial direction of said motor along an elongated slot formed in said base member.

6. A polishing unit as claimed in claim 1, wherein said motor is rotatable at either high or low speed.

7. A polishing unit as claimed in claim 1, wherein said grindstone rod section of said rotary grindstone assembly has a diameter of 4 to 6 mm.

8. A polishing unit as claimed in claim 1, wherein:
   (a) said supporting plate includes a plurality of grooves for supporting the root of working means extending from a grip of a dental instrument and
   (b) said supporting plate is movable along the sides of said base member.

9. A polishing unit as claimed in claim 1, wherein said at least one groove is parallel to said face of said grindstone disc section facing away from said motor.

10. A polishing unit as claimed in claim 9, wherein said supporting plate further includes at least one groove for supporting a second portion of the dental instrument while the dental instrument is being ground by said face of said grindstone disc section facing away from said motor that is perpendicular to said face of said grindstone disc section facing away from said motor.

11. A polishing unit as claimed in claim 1, wherein said at least one groove is perpendicular to said face of said grindstone disc section facing away from said motor.

* * * * *